United States Patent [19]

Kung et al.

[11] Patent Number: 5,196,310

[45] Date of Patent: * Mar. 23, 1993

[54] HYBRID CELL LINE FOR PRODUCING MONOCLONAL ANTIBODY TO A HUMAN MONOCYTE ANTIGEN, ANTIBODY, AND METHODS

[75] Inventors: Patrick C. Kung, Bridgewater; Gideon Goldstein, Short Hills, both of N.J.

[73] Assignee: Ortho Pharmaceutical Corporation, Raritan, N.J.

[*] Notice: The portion of the term of this patent subsequent to Mar. 27, 2007 has been disclaimed.

[21] Appl. No.: 389,246

[22] Filed: Aug. 3, 1989

Related U.S. Application Data

[60] Continuation of Ser. No. 763,330, Aug. 8, 1985, Pat. No. 4,912,045, which is a continuation of Ser. No. 432,456, Oct. 4, 1982, abandoned, which is a division of Ser. No. 110,509, Jan. 8, 1980, Pat. No. 4,364,936.

[51] Int. Cl.$^5$ ............................................. G01N 33/577
[52] U.S. Cl. .................................. 435/7.24; 436/548; 935/110
[58] Field of Search ..................... 424/85.8; 435/7.24; 436/548; 935/110

[56] References Cited

U.S. PATENT DOCUMENTS 4,364,936 12/1982 Kung et al. .......................... 424/85

OTHER PUBLICATIONS

Reinherz et al., Journal of Experimental Medicine, 151, pp. 969-974 (1980).
Brown et al., European Journal of Immunology 9, pp. 272-275 (1979).
Breard et al., The Journal of Immunology 124(4), pp. 1943-1948 (1980).
Ugolini et al., Proceedings of the National Academy of Sciences 77(11) pp. 6764-6768 (1980).
Springer et al., European Journal of Immunology 9, pp. 301-306 (1979).
Hurrell, Monoclonal Hybridoma Antibodies: Techniques and Applications 1982, pp. 181-186.
Todd et al., The Journal of Immunology, vol. 126, No. 4, Apr. 1981, pp. 1435-1441.
Reinherz, E. L. et al., "Separation of Functional subsets of human T cells by a monoclonal antibody", Proc Natl Acad. Sci., vol. 76, No. 8, pp. 4061-4065, Aug. 1979.

*Primary Examiner*—David Sauders
*Attorney, Agent, or Firm*—Gale F. Matthews; Geoffrey G. Dellenbaugh

[57] ABSTRACT

Hybrid cell line for production of monoclonal antibody to an antigen found on normal human monocytes and granulocytes. The hybrid is formed by fusing splenocytes from immunized BALB/cJ mice with P3X63Ag-8U1 myeloma cells. Diagnostic and therapeutic uses of the monoclonal antibody are also disclosed.

1 Claim, 3 Drawing Sheets

HYBRID CELL LINE FOR PRODUCING MONOCLONAL ANTIBODY TO A HUMAN MONOCYTE ANTIGEN, ANTIBODY, AND METHODS

This is a continuation of application Ser. No. 763,330, filed Aug. 8, 1985, now U.S. Pat. No. 4,912,045 which is a continuation of Ser. No. 432,456, filed on Oct. 4, 1982, now abandoned, which is a division of Ser. No. 110,509, filed on Jan. 8, 1980, now U.S. Pat. No. 4,364,936.

FIELD OF THE INVENTION

This invention relates generally to new hybrid cell lines and more specifically to hybrid cell lines for production of monoclonal antibody to an antigen found on normal human monocytes and granulocytes, to the antibody so produced, and to therapeutic and diagnostic methods and compositions employing this antibody.

DESCRIPTION OF THE PRIOR ART

The fusion of mouse myeloma cells to spleen cells from immunized mice by Kohler and Milstein in 1975 [*Nature* 256, 495-497 (1975)] demonstrated for the first time that it was possible to obtain a continuous cell line making homogeneous (so-called "monoclonal") antibody. Since this seminal work, much effort has been directed to the production of various hybrid cells (called "hybridomas") and to the use of the antibody made by these hybridomas for various scientific investigations. See, for example, *Current Topics in Microbiology and Immunology*, Volume 81-"Lymphocyte Hybridomas", F. Melchers, M. Potter, and N. Warner, Editors, Springer-Verlag, 1978, and references contained therein; C. J. Barnstable, et al., *Cell*, 14, 9-20 (May, 1978); P. Parham and W. F. Bodmer, *Nature* 276, 397-399 (November, 1978); *Handbook of Experimental Immunology*, Third Edition, Volume 2, D. M. Wier, Editor, Blackwell, 1978, Chapter 25; and *Chemical and Engineering News*, Jan. 1, 1979, 15-17. These references simultaneously indicate the rewards and complications of attempting to produce monoclonal antibody from hybridomas. While the general technique is well understood conceptually, there are many difficulties met and variations required for each specific case. In fact, there is no assurance, prior to attempting to prepare a given hybridoma, that the desired hybridoma will be obtained, that it will produce antibody if obtained, or that the antibody so produced will have the desired specificity. The degree of success is influenced principally by the type of antigen employed and the selection technique used for isolating the desired hybridoma.

The attempted production of monoclonal antibody to human lymphocyte cell-surface antigens has been reported only in a few instances. See, for example, *Current Topics in Microbiology and Immunology*, ibid, 66-69 and 164-169. The antigens used in these reported experiments were cultured human lymphoblastoid leukemia and human chronic lymphocytic leukemia cell lines. Many hybridomas obtained appeared to produce antibody to various antigens on all human cells. None of the hybridomas produced antibody against a predefined class of human lymphocytes.

More recently, the present applicants and others have authored articles disclosing the preparation and testing of hybridomas making antibody to certain T-cell antigens. See, for example, Reinherz, E. L., et al., J. Immunol. 123, 1312-1317 (1979); Reinherz, E. L., et al., Proc. Natl. Acad. Sci., 76, 4061-4065 (1979); and Kung, P. C., et al., Science, 206, 347-349 (1979).

Additionally, there has been a recent report of production of an anti-macrophage producing clone. See Springer, et al., Eur. J. Immunol., 9, 301 (1979).

It should be understood that there are two principal classes of lymphocytes involved in the immune system of humans and animals. The first of these (the thymus-derived cell or T cell) is differentiated in the thymus from haemopoietic stem cells. While within the thymus, the differentiating cells are termed "thymocytes." The mature T cells emerge from the thymus and circulate between the tissues, lymphatics, and the bloodstream. These T cells form a large proportion of the pool of recirculating small lymphocytes. They have immunological specificity and are directly involved in cell-mediated immune responses (such as graft rejection) as effector cells. Although T cells do not secrete humoral antibodies, they are sometimes required for the secretion of these antibodies by the second class of lymphocytes discussed below. Some types of T cells play a regulating function in other aspects of the immune system. The mechanism of this process of cell cooperation is not yet completely understood.

The second class of lymphocytes (the bone marrow-derived cells or B cells) are those which secrete antibody. They also develop from haemopoietic stem cells, but their differentiation is not determined by the thymus. In birds, they are differentiated in an organ analogous to the thymus, called the Bursa of Fabricius. In mammals, however, no equivalent organ has been discovered, and it is thought that these B cells differentiate within the bone marrow.

It is now recognized that T cells are divided into at least several subtypes, termed "helper", "suppressor", and "killer" T cells, which have the function of (respectively promoting a reaction, suppressing a reaction, or killing (lysing) foreign cells. These subclasses are well understood for murine systems, but they have only recently been described for human systems. See, for example, R. L. Evans, et al., *Journal of Experimental Medicine*, Volume 145, 221-232, 1977; and L. Chess and S. F. Schlossman—"Functional Analysis of Distinct Human T-Cell Subsets Bearing Unique Differentiation Antigens", in *"Contemporary Topics in Immunobiology"*, O. Stutman, Editor, Plenum Press, 1977, Volume 7, 363-379.

The ability to identify or suppress classes or subclasses of T cells is important for diagnosis or treatment of various immunoregulatory disorders or conditions.

For example, certain leukemias and lymphomas have differing prognosis depending on whether they are of B cell or T cell origin. Thus, evaluation of the disease prognosis depends upon distinguishing between these two classes of lymphocytes. See, for example, A. C. Aisenberg and J. C. Long, *The American Journal of Medicine*, 58:300 (March, 1975); D. Belpomme, et al., in *"Immunological Diagnosis of Leukemias and Lymphomas"*, S. Thierfelder, et al., eds, Springer, Heidelberg, 1977, 33-45; and D. Belpomme, et al., *British Journal of Haematology*, 1978, 38, 85.

Certain disease states (e.g., juvenile rheumatoid arthritis, malignancies, and agammaglobulinemia) are associated with an imbalance of T cell subclasses. It has been suggested that autoimmune diseases generally are associated with an excess of "helper" T cells or a deficiency of certain "suppressor" T cells, while agammaglobulinemia is associated with an excess of certain "suppressor" T cells or a deficiency of "helper" T cells. Malignancies generally are associated with an excess of "suppressor" T cells.

In certain leukemias, excess T cells are produced in an arrested stage of development. Diagnosis may thus depend on the ability to detect this imbalance or excess and to determine which developmental stage is in excess. See, for example, J. Kersey, et al., "Surface Markers Define Human Lymphoid Malignancies with Differing Prognoses" in *Haematology and Blood Transfusion*, Volume 20, Springer-Verlag, 1977, 17–24, and references contained therein; and E. L. Reinherz, et al., J. Clin. Invest., 64, 392–397 (1979).

Acquired agammaglobulinemia, a disease state in which no immune globulin is produced, comprises at least two distinct types. In type I the failure to produce immune globulin is due to an excess of suppressor T cells, while in type II it is due to a lack of helper T cells. In both types, there appears to be no defect or lack in the patients' B cells, the lymphocytes which are responsible for the actual secretion of the antibody; however, these B cells are being either suppressed or "not helped", resulting in greatly decreased or absent immune globulin production. The type of acquired agammaglobulinemia may thus be determined by testing for an excess of suppressor T cells or an absence of helper T cells.

On the therapeutic side, there is some suggestion, as yet not definitely proven, that administration of antibodies against the subtype of T cell in excess may have therapeutic benefit in autoimmune disease or malignancies. For example, a helper T cell cancer (certain cutaneous T cell lymphomas and certain T cell acute lymphoblastic leukemias) may be treated by an antibody to a helper T cell antigen. Treatment of autoimmune disease caused by an excess of helper cells may also be accomplished in the same fashion. Treatment of diseases (e.g., malignancies or type I acquired agammaglobulinemia) due to an excess of suppressor T cells may be treated by administration of an antibody to a suppressor T cell antigen.

Antisera against the entire class of human T cells (so-called antihuman thymocyte globulin or ATG) has been reported useful therapeutically in patients receiving organ transplants. Since the cell-mediated immune response (the mechanism whereby transplants are rejected) depends upon T cells, administration of antibody to T cells prevents or retards this rejection process. See, for example, Cosimi, et al., "Randomized Clinical Trial of ATG in Cadaver Renal Allgraft Recipients: Importance of T Cell Monitoring", *Surgery* 40:155-163 (1976) and references contained therein.

Lymphocytes, however, comprise only one class of leukocyte. The other two classes, granulocytes and monocytes, are also important in the function of the immune systems of humans and animals. In particular, macrophages, which are a type of monocytes, are extensively involved in immune function. For example, although macrophages themselves do not secrete antibody, they have been found necessary for the cooperation of T cells in the production of antibody by B cells.

Macrophages are also required for the generation of cytotoxic T cells and for the occurrence of a proliferative response by T cells in reaction to mitogens such as PHA or Con A. Although there has been speculation about the function of the macrophage in these processes, its precise role is not known. See, for example, E. S. Golub, *The Cellular Basis of the Immune Response*, Sinauer Associates, Sunderland, Mass., 1977, pages 146–158.

The identification and suppression of human T cell and monocyte classes and subclasses has previously been accomplished by the use of spontaneous autoantibodies or selective antisera for human T cells obtained by immunizing animals with human T cells, bleeding the animals to obtain serum, and adsorbing the antiserum with (for example) autologous but not allogeneic B cells to remove antibodies with unwanted reactivities. The preparation of these antisera is extremely difficult, particularly in the adsorption and purification steps. Even the adsorbed and purified antisera contain many impurities in addition to the desired antibody, for several reasons. First, the serum contains millions of antibody molecules even before the T cell immunization. Second, the immunization causes production of antibodies against a variety of antigens found on all human T cells injected. There is no selective production of antibody against a single antigen. Third, the titer of specific antibody obtained by such methods is usually quite low, (e.g., inactive at dilutions greater than 1:100) and the ratio of specific to non-specific antibody is less than $1/10^6$.

See, for example, the Chess and Schlossman article referred to above (at pages 365 and following) and the Chemical and Engineering News article referred to above, where the deficiencies of prior art antisera and the advantages of monoclonal antibody are described.

SUMMARY OF INVENTION

There has now been discovered a novel hybridoma (designated OKM1) which is capable of producing novel monoclonal antibody against an antigen found on normal human peripheral blood monocytes and granulocytes but not on normal human peripheral lymphoid cells (T cells, B cells, or null cells), thymocytes, lymphoblastoid cell lines, or tumor cells of T or B cell lineage.

The antibody so produced is monospecific for a single determinant on normal human peripheral blood monocytes and granulocytes and contains essentially no other anti-human immune globulin, in contrast to prior art antisera (which are inherently contaminated with antibody reactive to numerous human antigens) and to prior art monoclonal antibodies (which are not monospecific for a human monocyte antigen). Moreover, this hybridoma can be cultured to produce antibody without the necessity of immunizing and killing animals, followed by the tedious adsorption and purification steps necessary to obtain even the impure antisera of the prior art.

It is accordingly one object of this invention to provide hybridomas which produce antibodies against an antigen found on normal human peripheral blood monocytes and granulocytes.

It is a further aspect of the present invention to provide methods for preparing these hybridomas.

A further object of the invention is to provide essentially homogeneous antibody against an antigen found on normal human peripheral blood monocytes and granulocytes.

A still further object is to provide methods for treatment or diagnosis of disease or for identification of monocyte subclasses employing this antibody.

Other objects and advantages of the invention will become apparent from the examination of the present disclosure.

In satisfaction of the foregoing objects and advantages, there is provided by this invention a novel hybridoma producing novel antibody to an antigen found on normal human peripheral blood monocytes and granulocytes (but not on normal human peripheral lymphoid cells, thymocytes, lymphoblastoid cell lines or tumor cells of T or B cell lineage), the antibody itself, and diagnostic and therapeutic methods employing the antibody. The hybridoma was prepared generally following the method of Milstein and Kohler. Following immunization of mice with normal E rosette purified human mononuclear cells, the immunized mice were fused with cells from a mouse myeloma line and the resultant hybridomas screened for those with supernatants containing antibody which gave selective binding to normal E rosette positive and E rosette negative human peripheral blood lymphocyte populations. The desired hybridomas were subsequently cloned and characterized. As a result, a hybridoma was obtained which produces antibody (designated OKM1) against an antigen on normal human peripheral blood monocytes.

In view of the difficulties indicated in the prior art and the lack of success reported using malignant cell lines as the antigen, it was surprising that the present method provided the desired hybridoma. It should be emphasized that the unpredictable nature of hybrid cell preparation does not allow one to extrapolate from one antigen or cell system to another. In fact, the present applicants have discovered that the use of a T cell malignant cell line or purified antigens separated from the cell surface as the antigen were generally unsuccessful.

Both the subject hybridoma and the antibody produced thereby are identified herein by the designation "OKM1", the particular material referred to being apparent from the context. The subject hybridoma was deposited on Dec. 13, 1979, at the American Type Culture Collection, 12301 Parklawn Drive, Rockville, Md. 20852, and was given the ATCC accession number CRL 8026.

The preparation and characterization of the hybridoma and the resultant antibody will be better understood by reference to the following description and Examples.

DETAILED DESCRIPTION OF THE INVENTION

The method of preparing the hybridoma generally comprises the following steps:

A. Immunizing mice with normal human peripheral blood mononuclear cells. While it has been found that female BALB/cJ mice are preferred, it is contemplated that other mouse strains could be used. The immunization schedule and thymocyte concentration should be such as to produce useful quantities of suitably primed splenocytes. Three immunizations at fourteen day intervals with $2 \times 10^7$ cells/mouse/injection in 0.2 ml phosphate buffered saline has been found to be effective.

B. Removing the spleens from the immunized mice and making a spleen suspension in an appropriate medium. About one ml of medium per spleen is sufficient. These experimental techniques are well-known.

C. Fusing the suspended spleen cells with mouse myeloma cells from a suitable cell line by the use of a suitable fusion promoter. The preferred ratio is about 5 spleen cells per myeloma cell. A total volume of about 0.5–1.0 ml of fusion medium is appropriate for about $10^8$ splenocytes. Many mouse myeloma cell lines are known and available, generally from members of the academic community or various deposit banks, such as the Salk Institute Cell Distribution Center, La Jolla, Calif. The cell line used should preferably be of the so-called "drug resistant" type, so that unfused myeloma cells will not survive in a selective medium, while hybrids will survive. The most common class is 8-azaguanine resistant cell lines, which lack the enzyme hypoxanthine guanine phophoribosyl transferase and hence will not be supported by HAT (hypoxanthine, aminopterin, and thymidine) medium. It is also generally preferred that the myeloma cell line used be of the so-called "non-secreting" type, in that it does not itself produce any antibody, although secreting types may be used. In certain cases, however, secreting myeloma lines may be preferred. While the preferred fusion promoter is polyethylene glycol having an average molecular weight from about 1000 to about 4000 (commercially available as PEG 1000, etc.), other fusion promoters known in the art may be employed.

D. Diluting and culturing in separate containers, the mixture of unfused spleen cells, unfused myeloma cells, and fused cells in a selective medium which will not support the unfused myeloma cells for a time sufficient to allow death of the unfused cells (about one week). The dilution may be a type of limiting one, in which the volume of diluent is statistically calculated to isolate a certain number of cells (e.g., 1–4) in each separate container (e.g., each well of a microtiter plate). The medium is one (e.g., HAT medium) which will not support the drug resistant (e.g., 8-azaguanine resistant) unfused myeloma cell line. Hence, these myeloma cells perish. Since the unfused spleen cells are non-malignant, they have only a finite number of generations. Thus, after a certain period of time (about one week) these unfused spleen cells fail to reproduce. The fused cells, on the other hand, continue to reproduce because they possess the malignant quality of the myeloma parent and the ability to survive in the selective medium of the spleen cell parent.

E. Evaluating the supernatant in each container (well) containing a hybridoma for the presence of antibody to E rosette positive purified or E rosette negative human peripheral blood lymphocytes.

F. Selecting (e.g., by limiting dilution) and cloning hybridomas producing the desired antibody.

Once the desired hybridoma has been selected and cloned, the resultant antibody may be produced in one of two ways. The purest monoclonal antibody is produced by in vitro culturing of the desired hybridoma in a suitable medium for a suitable length of time, followed by recovery of the desired antibody from the supernatant. The suitable medium and suitable length of culturing time are known or are readily determined. This in vitro technique produces essentially monospecific monoclonal antibody, essentially free from other specific antihuman immune globulin. There is a small amount of other immune globulin present since the medium contains xenogeneic serum (e.g., fetal calf serum). However, this in vitro method may not produce a sufficient quantity or concentration of antibody for some purposes, since the concentration of monoclonal antibody is only about 50 µg/ml.

To produce a much greater concentration of slightly less pure monoclonal antibody, the desired hybridoma may be injected into mice, preferably syngenic or semi-syngenic mice. The hybridoma will cause formation of antibody-producing tumors after a suitable incubation time, which will result in a high concentration of the desired antibody (about 5-20 mg/ml) in the bloodstream and peritoneal exudate (ascites) of the host mouse. Although these host mice also have normal antibodies in their blood and ascites, the concentration of these normal antibodies is only about 5% of the monoclonal antibody concentration. Moreover, since these normal antibodies are not antihuman in their specificity, the monoclonal antibody obtained from the harvested ascites or from the serum is essentially free of any contaminating antihuman immune globulim. This monoclonal antibody is high titer (active at dilutions of 1:50,000 or higher) and high ratio of specific to nonspecific immune globulin (about 1/20). Immune globulin produced incorporating the light myeloma chains are non-specific, "nonsense" peptides which merely dilute the monoclonal antibody without detracting from its specificity.

EXAMPLE I

Production of Monoclonal Antibodies

A. Immunization and Somatic Cell Hybridization

Female BALB/cJ mice (Jackson Laboratories; 6-8 weeks old) were immunized intraperitoneally with $2 \times 10^7$ rosette purified human mononuclear cells in 0.2 ml of phosphate buffered saline at 14-day intervals. Four days after the third immunization, spleens were removed from the mice, and a single cell suspension was made by pressing the tissue through a stainless steel mesh.

Cell fusion was carried out according to the procedure developed by Kohler and Milstein. $1 \times 10^8$ splenocytes were fused in 0.5 ml of a fusion medium comprising 35% polyethylene glycol (PEG 1000) and 5% dimethylsulfoxide in RPMI 1640 medium (Gibco, Grand Island, N.Y.) with $2 \times 10^7$ P3X63Ag8U1 myeloma cells supplied by Dr. M. Scharff, Albert Einstein College of Medicine, Bronx, N.Y. These myeloma cells secrete $IgG_1$ light chains.

B. Selection and Growth of Hybridoma

After cell fusion, cells were cultured in HAT medium (hypoxanthine, aminopterin, and thymidine) at 37° C. with 5% $CO_2$ in a humid atmosphere. Several weeks later, 40 to 100 l of supernatant from cultures containing hybridomas were added to a pellet of $10^6$ peripheral lymphocytes separated into E rosette positive (E+) and E rosette negative (E−) populations, which were prepared from blood of healthy human donors as described by Mendes (J. Immunol. 111:860, 1973). Detection of mouse hybridoma antibodies binding to these cells was determined by indirect immunofluorescence. Cells incubated with culture supernatants were stained with a fluorescinated goat-anti-mouse IgG (G/M FITC) (Meloy Laboratories, Springfield, Va.; F/p =2.5) and the fluorescent antibody-coated cells were subsequently analyzed on the Cytofluorograf FC200/4800A (Ortho Instruments, Westwood, Mass.) as described in Example III. Hybridoma cultures containing antibodies reacting specifically with E+ lymphocytes (T cells) and/or E− lymphocytes were selected and cloned twice by limiting dilution methods in the presence of feeder cells. Subsequently, the clones were transferred intraperitoneally by injecting $1 \times 10^7$ cells of a given clone (0.2 ml volume) into BALB/cJ mice primed with 2,6,10,14-tetramethylpentadecane, sold by Aldrich Chemical Company under the name Pristine. The malignant ascites from these mice were then used to characterize mononuclear cells as described below in Example II.

The monoclonal antibody produced by one of these clones, which reacted with a fraction of both E+ and E− cells, was termed OKM1. The subject hybrid antibody OKM1 was demonstrated by standard techniques to be of $IgG_{2a}$ subclass.

EXAMPLE II

Characterization of OKM1 Reactivity

A. Isolation of Mononuclear Cell Populations

Human peripheral blood mononuclear cells were isolated from healthy volunteer donors (ages 15-40) by Ficoll-Hypaque density gradient centrifugation (Pharmacia Fine Chemicals, Piscataway, N.J.) following the technique of Boyum, Scand. J. Clin. Lab. Invest. 21 (Suppl. 97): 77, 1968.

Adherent cells were obtained by a one hour incubation of mononuclear cells in polystyrene dishes ($100 \times 20$ mm tissue culture dishes) (Falcon, Oxnard, Calif.) in RPMI 1640 (Grand Island Biological Company, Grand Island, N.Y.) supplemented with 20% pooled human AB serum. After removal of the non-adherent fraction, adherent cells were detached by incubation at 4° C. in serum-free MEM, 2.5 mM EDTA, followed by gentle scraping with the rubber tip of a disposable syringe plunger.

Mononuclear cells were separated into E+ and E− populations by rosetting with sheep erythrocytes and differential centrifugation over Ficoll-Hypaque. Rosetting was accomplished by centrifugation of the mononuclear cells/sheep erythrocyte mixture for five minutes at 800 rpm and incubating for one hour at 4° C. The erythrocyte: lymphocyte ratio was 40:1. The E+ cells were recovered by lysis of the sheep erythrocytes with a 0.85% ammonium chloride solution.

Null cells were prepared by similar rosetting on the surface immunoglobulin negative (sIg−) population obtained by Sephadex G-200 anti-human ($F(ab^1)_2$) chromatography as previously described by Chess, et al., J. Immunol., 113:1113 (1974). Polymorphonuclear leukocytes were obtained by lysis of the erythrocytes present in the pellet formed during Ficoll Hypaque centrifugation of peripheral blood.

B. Isolation of Thymocytes

Normal human thymus gland was obtained from patients aged two months to 14 years undergoing corrective cardiac surgery. Freshly obtained portions of the thymus gland were immediately placed in 5% fetal calf serum in medium 199 (Gibco), finely minced with forceps and scissors, and subsequently made into single cell suspensions by being pressed through wire mesh. The cells were next layered over Ficoll-Hypaque and spun and washed as previously described in section A above. The thymocytes so obtained were >95% viable and ≧90% E rosette positive.

C. Cell Lines of T Lineage and T Acute Lymphoblastic Leukemia Cells.

T cell lines CEM and HSB-2, and B cell lines Laz 156 and Laz 388 were provided by Dr. H. Lazarus (Sidney Farber Cancer Institute, Boston, Mass.). Leukemic cells were obtained from patients with the diagnosis of acute myelomonocytic leukemia (AMML; 5 patients) and acute myeloblastic leukemia (AML; 8 patients). Tumor populations were cryopreserved at −196° C. vapor phase liquid nitrogen with 10% DMSO and 20% AB human serum until the time of surface characterization.

EXAMPLE III

Cytofluorographic Analysis and Cell Separation

Cytofluorographic analysis of monoclonal antibodies with all cell populations was performed by indirect immunofluorescence with fluorescein-conjugated goat anti-mouse IgG (G/M FITC) (Meloy Laboratories) utilizing a Fluorescence Activated Cell Sorter (FACS-I) (Becton, Dickinson, Mountain View, Calif.) or a Cytofluorograf FC200/4800A (Ortho Instruments). In brief, $1 \times 10^6$ cells were treated with 0.15 ml OKM1 at a 1:500 dilution, incubated at 4° C. for 30 minutes, and washed twice. The cells were then reacted with 0.15 ml of a 1:40 dilution G/M FITC at 4° C. for 30 minutes, centrifuged, and washed twice. Cells were then analyzed on the FACS-I and the intensity of fluorescence per cell was recorded on a pulse height analyzer. Background staining was obtained by substituting a 0.15 ml aliquot of 1:500 ascites from a BALB/cJ mouse intraperitoneally injected with a non-producing hybrid clone.

In experiments involving antibody and complement mediated lympholysis, thymocytes and peripheral T cells were cultured overnight following selective lysis and then subsequently analyzed on the Cytofluorograf or FACS.

A. Cytotoxicity Studies

Sensitization cultures for cell-mediated lympholysis (CML) were established by the following procedure. Five $\times 10^6$ target cells were treated with 0.2 ml $^{51}$Cr sodium chromate (292 μCi/ml) (New En9land Nuclear, Boston, Mass.) and incubated for 90 minutes at 37° C. After two washes, the cells were diluted to $2 \times 10^5$/ml in media containing 10% FCS. Twenty 1 of labeled cells were distributed in conical microplate wells with 20 μl of serial dilutions of hybridoma antibody. Following a one hour incubation at 4° C., 20 μl fresh rabbit serum (1:10 dilution) were added to the wells as a source of complement. The plates were incubated at 37° C. for one hour. One hundred forty μl of media were then added to the wells and the plates were spun at 400 g for 10 minutes. One hundred μl of supernatant were removed from each well and counted on a gamma scintillation counter (Parkard Instrumentation Company, Downer's Grove, Ill.). Specific $^{51}$Cr release was calculated using the following formula:

$$\% \text{ specific }^{51}CR \text{ release} = \frac{Exp - SR}{MR - SR} \times 100$$

where Exp=mean of the observed triplicate, SR=spontaneous release from the cells incubated with complement alone, and MR=maximum release obtained by treating the cells with the detergent Triton X (1% solution)

Lysis of larger number of cells for subsequent proliferative assays was done by resuspending 20 to $50 \times 10^6$ mononuclear cells in 1 ml of OKM1 at a 1:250 dilution and incubating at 4° C. for one hour.

Subsequently, 0.1 ml fresh rabbit serum was added and the cells further incubated at 37° C. for one hour. After three washes, the cells were counted and their viability was assessed by Trypan blue exclusion.

B. Proliferative Response Assay

The proliferative response to soluble antigens was measured as previously described. Cells were brought up at a concentration of $2 \times 10^6$ viable cells/ml in RPMI 1640 supplemented with 20% human AB serum and cultured in microtiter plates in the presence of tetanus toxoid (TT) (Massachusetts Department of Public Health Biological Laboratories, Boston, Mass.), purified protein derivative (PPD) (National Institutes of Health, Bethesda, Md.), or mumps CF antigen (Microbiological Associates, Walkersville, Md.). The cultures were pulsed after five days with 0.2 Ci of [H-methyl] thymidine ($^3$H TdR) (1.9 μCi/mM specific activity) (Schwarz-Mann, Orangeburg, N.Y.) and harvested 18 hours later on a MASH 11 apparatus (Microbiological Associates). $^3$H-TdR incorporation was measured in a Packard Liquid Scintillation Counter (Packard Instrumentation Company). Each experimental group was assayed in triplicate and the results are expressed as mean counts per minute (cpm)±the standard error of the mean.

The production of the hybridoma and the production and characterization of the resulting monoclonal antibody were conducted as described in the above Examples. Although large quantities of the subject antibody were prepared by injecting the subject hybridoma intraperitoneally into mice and harvesting the malignant ascites, it is clearly contemplated that the hybridoma could be cultured in vitro by techniques well-known in the art and the antibody removed from the supernatant.

Figure 1A:
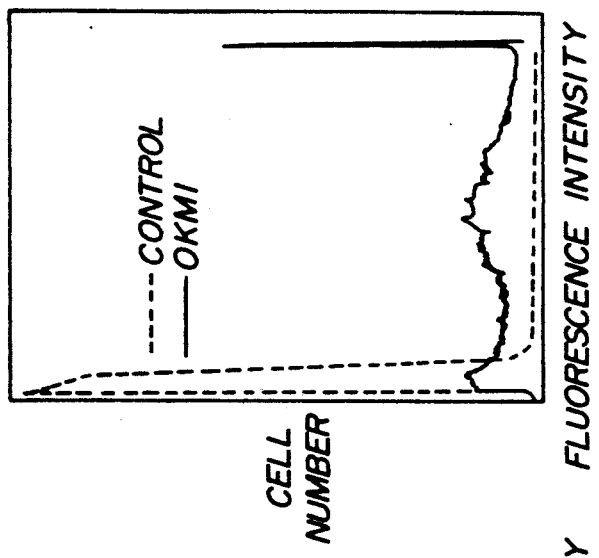
FIG. 1 shows the fluorescence pattern obtained on the FACS after reacting unfractionated (FIG. 1A), nonadherent (FIG. 1B), and adherent (FIG. 1C) normal human peripheral blood mononuclear cells from donor #1 with OKM1 at a 1:500 dilution and G/M FITC. Background fluorescence staining was obtained by incubating each population with a 1:500 dilution of ascitic fluid from a mouse injected with a non-producing clone.
Figure 1B:
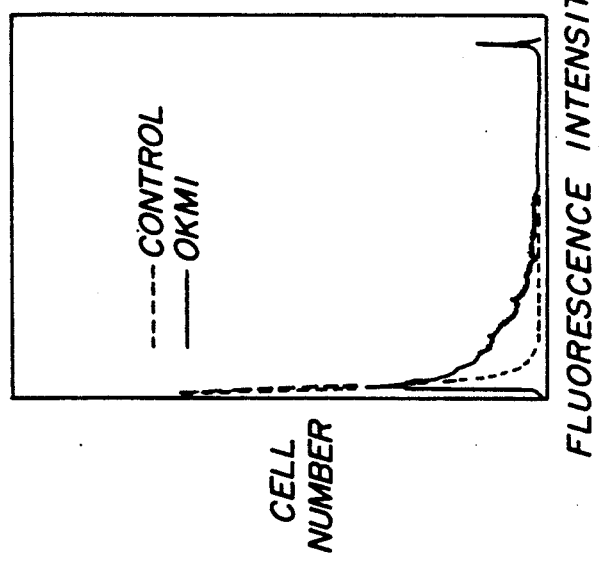
Figure 1C:
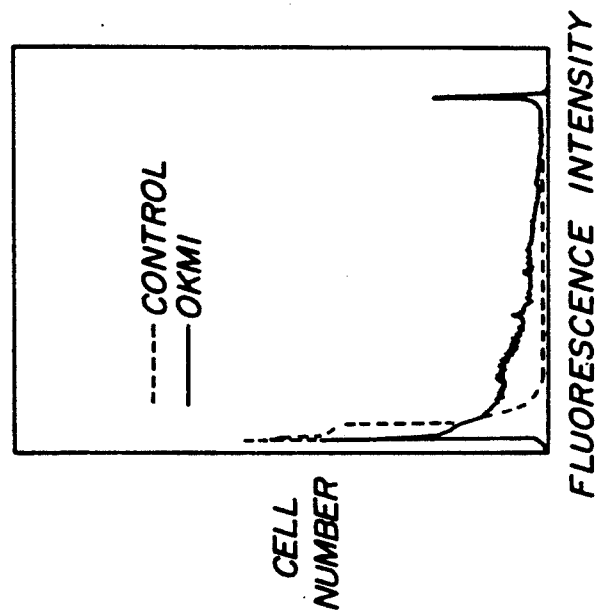

Peripheral blood mononuclear cells of nine normal donors were separated into adherent and nonadherent populations on polystyrene dishes, and each fraction was analyzed by indirect immunofluorescence on the FACS. The percentages of cells specifically labeled by OKM1 are given in Table I. The mean of positive cells was 27% for unfractionated cells, 18% for nonadherent cells, and 78% for adherent cells. The FACS fluorescence profiles of the three populations for donor #1 are illustrated in FIG. 1. As seen in FIG. 1A, the fluorescence pattern of OKM1 on unfractionated mononuclear cells is bimodal. A two dimensional mapping of the same population showed that the cells brightly stained by OKM1 are also larger. A population of smaller cells with a weaker fluorescence intensity was also detected. Most of these smaller cells are found in the nonadherent fraction (FIG. 1B). Adherent cells, in contrast, contain the brightly stained larger pupulation (FIG. 1C). This reactivity of OKM1 with adherent populations suggested that the mononuclear cell recognized by the antibody was a monocyte and provides one test by which the subject antibody may be detected and distinguished from the antibodies.

The study of lymphoid and myeloid cells of different origins gave further evidence for this specificity. OKM1 was unreactive with B cell lines (Laz 156, and Laz 388), T cell lines (CEM and HSB 2), and three human thymocyte preparations. Moreover, three T-CLL, six B-CLL, three T-ALL, and six non T-ALL tumor cells were also negative. In contrast, OKM1 reacted strongly with 44 to 82% of the cells of five acute myelomonocytic leukemia (AMML) samples and with about 35% of the cells in two out of eight acute myeloblastic leukemia (AML) cases. Two myeloid lines, K562 (Lozzio, et al., Blood 45, 321 (1975) and HL 60 (Collins, et al., Native, 270 347 (1977) were negative. Isolated polymorphonuclear leukocytes from four normal donors were brightly labeled. These results were consistent with the notion of granulocytes and monocytes being closely related cells of common origin. In addition, the data obtained with AML cells seemed to indicate that OKM1 reacted preferentially with monocytic cells with the myeloid lineage. This pattern of reactivity provides an additional test by which the subject antibody may be detected and distinguished from other antibodies.

The staining pattern observed on unfractionated, adherent, and nonadherent mononuclear cells suggested that the monocyte population defined by the antibody was heterogeneous with respect to size and adherent properties. As surface Ia antigens have been described on subpopulations of monocytes, the above cell fractions (donor #1) were tested with a monoclonal anti-Ia antibody, OKI1, in order to characterize further the phenotype of the cells identified by OKM1. 1 The percentage of OKI1+ cells in the nonadherent and adherent fractions were 9% and 80% respectively. As Ia bearing B lymphocytes account for some of the staining found with OKI1 in nonadherent populations, it appeared that the small, nonadherent cell recognized by OKM1 is mainly Ia−. In contrast, the large, adherent OKM+ monocytes carry surface Ia determinants.

Figure 2A:
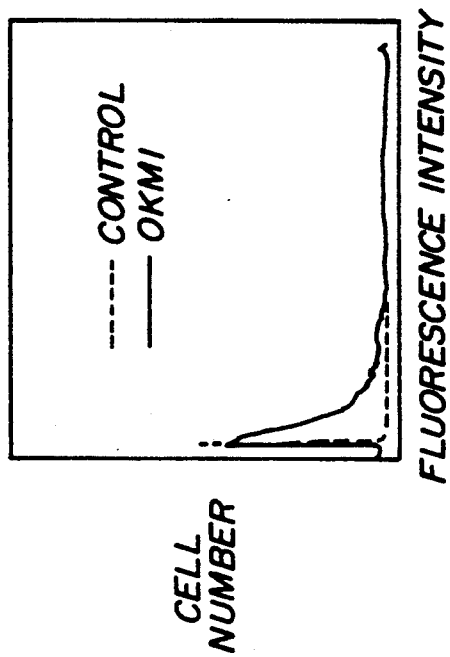
FIG. 2 shows the fluorescence obtained on the FACS after reacting normal human E+ (FIG. 2B) and E− (FIG. 2A) peripheral blood mononuclear cells with OKM1 and G/M FITC.
Figure 2B:
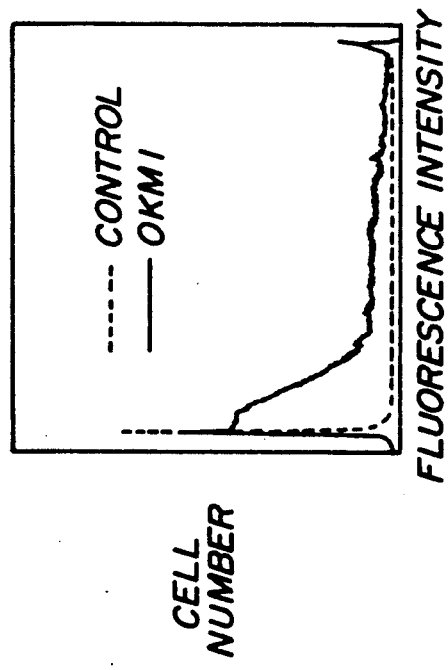

The distribution of OKM1 cells within E+ and E− populations is shown in Table II. Although most of the labeled cells were found in the E− population, up to 22% (mean, 13%) positive cells were present in the E+ fraction. FACS fluorescence profiles for E− and E+ cells are shown in FIG. 2. E− cells had a bimodal staining pattern due to the presence of the large and small cells described above. The fluorescence intensity on the E+ population was more homogeneous. The positive cells found in this fraction were of a small size and largely Ia− (mean reactivity with OKI1,3%). This pattern of reactivity is a further test by which the subject antibody may be detected and distinguished from other antibodies.

Figure 3:
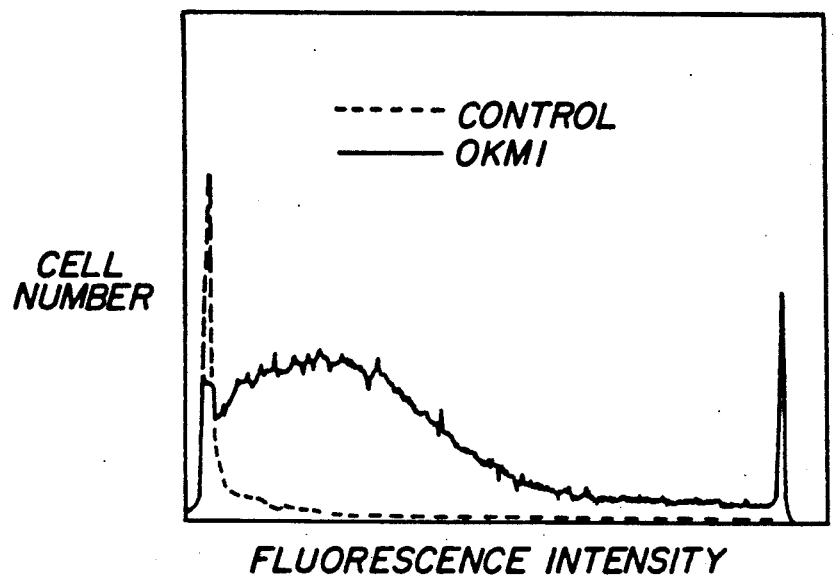
FIG. 3 shows the fluorescence pattern obtained on the FACS after reacting normal human Ig−, E−, nonadherent null cells with OKM1 and G/M FITC.

A representative FACS histogram of OKM1 reactivity with the Ig−, E−, nonadherent cell population is illustrated in FIG. 3. Eighty-four percent of the cells were stained with OKM1 and 11% with OKI1. Thus, these studies indicated that the OKM1+, Ia− nonadherent cell accounted surprisingly for most of the Null cell population. This pattern of reactivity is a still further test by which the subject antibody may be detected and distinguished from other antibodies.

Figure 4:
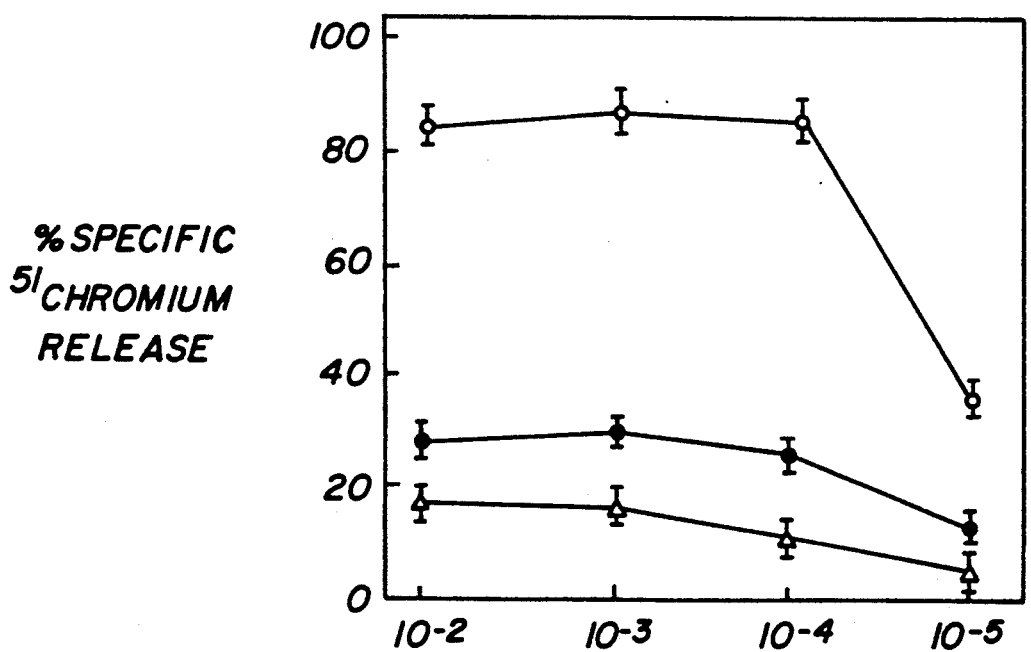
FIG. 4 shows the lytic capacity of OKM1 and complement on human mononuclear cells.

Complement mediated lysis assays were performed on several of the populations described above. Serial dilutions of OKM1 were tested on unfractionated, nonadherent, and adherent cells. Specific $^{51}Cr$ release values are shown in FIG. 4. There was a good correlation between the percentages found by indirect immunofluoresence (donor #5, Table I) and complement mediated lysis for each population.

E+ and E− cells were also studied and the data obtained are presented in Table III. Again, the specific $^{51}Cr$ release results corresponded to the labeling found by indirect immunofluorescence (donors #8, #9, and #10).

The effect of OKM1 and complement pretreatment on a known monocyte dependent T cell function, i.e., proliferation to soluble antigens, was studied. Mononuclear cells from a normal donor were incubated with OKM1 antibody (1:250 dilution) in the presence of complement. Graded amount of autologous adherent cells were added to this pre-treated population prior to triggering with soluble antigens. As shown in Table IV, OKM1 and complement treated mononuclear cells did not proliferate in response to soluble antigens, while the addition of 1% adherent cells could restore their proliferative response. As incubation with OKM1 antibodies in the absence of complement did not affect this T cell function, the effect seen in the presence of complement could be attributed to specific killing of monocytes within the mononuclear cell population.

It should be noted that, when 10 to 20% adherent cells were added to OKM1 pretreated cells, both the background and the antigen induced proliferation were increased when compared to the untreated population.

The effect of OKM1 on CML is also a test by which the subject antibody may be detected and distinguished from other antibodies.

Table V shows the relationship between levels of peripheral T cells and T cell subsets and various disease states. These relationships may be used for diagnostic purposes (e.g., to detect acute infectious mononucleosis) by analyzing the blood sample of an individual suspected of having one of these disease states to determine the levels of T cells and T cell subsets. These relationships may also be used for therapeutic purposes where the cause of the disease state is an elevated level of a T cell subset (e.g., Type I acquired agammaglobulinemia). For therapeutic use, administration of the appropriate monoclonal antibody to a patient with an elevated T cell subset level will decrease or eliminate the excess. The relationships shown in Table V are a further way in which OKT11 antibody may be detected and distinguished from other antibodies.

Other monoclonal antibody producing hybridomas prepared by the present applicants (designated OKT1, OKT3, OKT4, and OKT5) are described and claimed in the following U.S. patent applications: Ser. No. 22,132,filed Mar. 20, 1979, now U.S. Pat. No. 4,632,799; Ser. No. 33,639, filed Apr. 26, 1979, now U.S. Pat. No. 4,381,295; Ser. No. 33,669, filed Apr. 26, 1979, now U.S. Pat. No. 4,361,549; Ser. No. 76,642, filed Sep. 18, 1979; and Ser. No. 82,515, filed Oct. 9, 1979, now U.S. Pat. No. 4,364,932. Still other monoclonal antibody producing hybridomas prepared by the present applicants (designated OKT6, OKT8, OKT9, and OKT10) are described and claimed in U.S. patent applications filed on Dec. 4, 1979 and entitled:

Hybrid Cell Line for Producing Monoclonal Antibody to a Human Thymocyte Antigen, Antibody, and Methods; Hybrid Cell Line For Producing Complement-Fixing Monoclonal Antibody to Human Suppressor T Cells, Antibody, and Methods; Hybrid Cell Line For Producing Monoclonal Antibody to Human Early Thymocyte Antigen, Antibody, and Methods; and Hybrid Cell Line For Producing Monoclonal Antibody to a Human Prothymocyte Antigen, Antibody, and Methods. A further monoclonal antibody producing hybridoma prepared by the present applicants (designated OKT11) is described and claimed in a U.S. patent application filed on even date herewith and entitled: Hybrid Cell Line for Producing Antibody for a Human T Cell Antigen, Antibody, and Methods.

These applications are incorporated herein by reference.

According to the present invention there are provided a hybridoma capable of producing antibody against an antigen found on normal human monocytes, a method for producing this hybridoma, monoclonal antibody against an antigen found on normal human monocytes, methods for producing the antibody, and methods and compositions for treatment or diagnosis of disease or identification of monocyte subclasses employing this antibody.

TABLE I

Percentage of Cells Reactive with OKM1 by Indirect Immunofluorescence

| Donor | Percentage of Positive Cells | | |
|---|---|---|---|
| | F/H[a] | F/H Non Adherent | Adherent |
| 1 | 32.3 | 20.4 | 80.6 |
| 2 | 28.2 | 23.6 | 83.4 |
| 3 | 20.4 | 17.5 | 67.6 |
| 4 | 20.6 | 16.1 | 74.4 |
| 5 | 26.1 | 16.5 | 82.7 |
| 6 | 28.1 | 20.2 | 74.2 |
| 7 | 30.5 | ND | 84.8 |
| 8 | 27.7 | ND | 80.7 |
| 9 | 28.7 | 11.2 | 76.0 |
| Mean | 26.9 | 17.9 | 78.2 |

[a]Mononuclear cells prepared by centrifugation on Ficoll-Hypaque gradient.

TABLE II

Percentage of Cells Reactive with OKM1 in E Rosette Positive and E Rosette Negative Populations

| Donor | Percentage of Positive Cells | |
|---|---|---|
| | E+ | E− |
| 1 | 18.2 | 64.2 |
| 2 | 12.1 | 51.2 |
| 3 | 13.8 | 47.9 |
| 4 | 9.7 | 67.9 |
| 5 | 14.2 | 41.5 |
| 6 | 22.2 | 69.0 |
| 7 | 11.5 | 51.2 |
| 8 | 10.6 | 58.6 |
| 9 | 9.4 | 55.6 |
| 10 | 12.8 | 68.5 |
| Mean | 13.5 | 57.5 |

TABLE III

OKM1 Reactivity by Complement Mediated Lysis on E Rosette Positive and E Rosette Negative Populations

| Antibody Dilution | Percent Specific $^{51}$Cr Release | | |
|---|---|---|---|
| | Donor #8 | Donor #9 | Donor #10 |
| E+ | | | |
| $10^{-2}$ | 11.2 ± 3 | 9.8 ± 2 | 12.5 ± 1 |
| $10^{-3}$ | 7.8 ± 2 | 10.7 ± 2 | 11.7 ± 2 |
| $10^{-4}$ | 4.4 ± 2 | 9.0 ± 2 | 11.2 ± 2 |
| $10^{-5}$ | 1.5 ± 1 | 6.7 ± 1 | 5.5 ± 2 |
| E− | | | |
| $10^{-2}$ | 71.5 ± 4 | 68.7 ± 5 | 74.3 ± 5 |
| $10^{-3}$ | 73.0 ± 3 | 63.3 ± 7 | 70.6 ± 4 |
| $10^{-4}$ | 67.0 ± 5 | 57.3 ± 4 | 70.9 ± 3 |
| $10^{-5}$ | 56.7 ± 3 | 52.9 ± 3 | 60.2 ± 5 |

TABLE IV

Effect of Pretreatment of Mononuclear Cells with OKM1 and C' on Antigen Induced Proliferative Responses[a]
$^3$H-Thymidine Incorporation

| Cell Population | Media | TT | PPD | Mumps |
|---|---|---|---|---|
| F/H | 385 ± 88 | 1,767 ± 425 | 5,063 ± 1,010 | 19,094 ± 3,139 |
| F/H OKM1 + C' | 144 ± 10 | 142 ± 12 | 162 ± 23 | 254 ± 4 |
| F/H OKM1 + C' + 1% Adherent cells | 190 ± 51 | 1,358 ± 209 | 5,777 ± 1,013 | 7,269 ± 1,090 |
| ± 10% Adherent cells | 1,425 ± 259 | 4,128 ± 921 | 16,412 ± 2,747 | 38,558 ± 1,680 |
| ± 20% Adherent cells | 1,944 ± 665 | 5,926 ± 1,429 | 13,182 ± 3,007 | 40,065 ± 5,810 |
| Adherent cells | 192 ± 69 | 261 ± 186 | 224 ± 95 | 804 ± 42 |

[a]All cultures done in triplicate. Results expressed as mean counts per minute standard error of the mean
[b]TT (Tetanus Toxoid): 10 g/ml
[c]PPD (Purified Protein Derivative): 10 g/ml
[d]Mumps: 1/20 dilution

TABLE V

PERIPHERAL MONONUCLEAR CELL LEVELS IN DISEASE STATES

| Disease State | Monoclear Cell Levels | | | | | | |
|---|---|---|---|---|---|---|---|
| | OKT3+ | OKT4+ | OKT5 | OKT8 | OKT6 | OKT11 | OKM1 |
| Primary Biliary Cirrhosis (2) | N | + | − | − | − | ++ | − |
| Multiple Sclerosis (advanced disease) (8) | − | N | − | − | − | − | + |
| Myasthenia Gravis | O | O | O | O | O | − | + |

TABLE V-continued
PERIPHERAL MONONUCLEAR CELL LEVELS IN DISEASE STATES

| Disease State | Monoclear Cell Levels | | | | | | |
|---|---|---|---|---|---|---|---|
| | OKT3+ | OKT4+ | OKT5 | OKT8 | OKT6 | OKT11 | OKM1 |
| (early untreated) (3) | | | | | | | |
| Acute Graft vs Host (3) | O to − | − | O | + | + | + | − |
| Acquired Agamma globulinemia | | | | | | | |
| Type I | | | + | | | | |
| Type II | | O | | | | | |
| Hyper IgE (4) | − | N | O to − | O to − | − | + | N |
| Acute Infectious Mononucleosis (4)* | + | O to −− | ++ | ++ | O | ++ | − |
| Hodgkins Disease | | | | | | | |
| Stages I & II | N | N | N | N | O | O | N |
| Stages III & IV | −− | N | N | N | O | O | ++ |
| Psoriasis (3/5) | N | + to ++ | N | N | O | N | N |

N = within normal limits
O = absent
+ = above normal
++ = greatly above normal
− = below normal
−− = greatly below normal
*these levels return to normal about one week prior to the disappearance of clinical symptoms
The numbers in parentheses indicate the number of patients evaluated.

Although only a single hybridoma producing a single monoclonal antibody against a human thymocyte antigen is described, it is contemplated that the present invention encompasses all monoclonal antibodies exhibiting the characteristics described herein. It was determined that the subject antibody OKM1 belongs to the subclass IgG$_{2a}$, which is one of four subclasses of murine IgG. These subclasses of immune globulin G differ from one another in the so-called "fixed" regions, although an antibody to a specific antigen will have a so-called "variable" region which is functionally identical regardless of which subclass of immune globulin G it belongs to. That is, a monoclonal antibody exhibiting the characteristic described herein may be of subclass IgG$_1$, IgG$_{2a}$, IgG$_{2b}$, or IgG$_3$, or of classes IgM, IgA, or other known Ig classes. The differences among these classes or subclasses will not affect the selectivity of the reaction pattern of the antibody, but may affect the further reaction of the antibody with other materials, such as (for example) complement or anti-mouse antibodies. Although the subject antibody is specifically IgG$_{2a}$, it is contemplated that antibodies having the patterns of reactivity illustrated herein are included within the subject invention regardless of the immune globulin class or subclass to which they belong.

Further included within the subject invention are methods for preparing the monoclonal antibodies described above employing the hybridoma technique illustrated herein. Although only one example of a hybridoma is given herein, it is contemplated that one skilled in the art could follow the immunization, fusion, and selection methods provided herein and obtain other hybridomas capable of producing antibodies having the reactivity characteristics described herein. Since the individual hybridoma produced from a known mouse myeloma cell line and spleen cells from a known species of mouse cannot be further identified except by reference to the antibody produced by the hybridoma, it is contemplated that all hybridomas producing antibody having the reactivity characteristics described above are included within the subject invention, as are methods for making this antibody employing the hybridoma.

Further aspects of the invention are methods of treatment or diagnosis of disease employing the monoclonal antibody OKM1 or any other monoclonal antibody exhibiting the pattern of reactivity provided herein. The subject antibody may be used to detect and study monocyte differentiation. Moreover, the subject antibody may be employed to diagnose disease states as shown in Table V. These techniques may be employed using OKM1 antibody alone or in combination with other antibodies (e.g., OKT3-OKT11). Patterns of reactivity with a panel of antibodies to T cells and T cell subsets and/or monocyte subsets will allow more precise detection of certain disease states then is possible using prior diagnostic methods. As an example, AMML and (to a lesser extent) AML may be detected by reacting leukemia cells from individuals with OKM1 antibody.

Treatment of disease states (e.g., malignancies such as AMML) manifesting themselves as an excess of OKM1+ cells may be accomplished by administration of a therapeutically effective amount of OKM1 antibody to an individual in need of such treatment. By selective reaction with OKM+antigen, the effective amount of OKM1 antibody will reduce the excess of OKM1+ cells, thus ameliorating the effects of the excess.

Diagnostic and therapeutic compositions comprising effective amounts of OKM1 antibody in admixture with diagnostically or pharmaceutically acceptable carriers, respectively, are also included within the present invention.

What is claimed is:

1. A diagnostic composition of matter for detection of OKM1+ cell excess or deficiency comprising, in admixture with a diagonstically acceptable carrier, an amount of a monoclonal antibody effective to detect such OKM+ cell excess or deficiency, wherein said monoclonal antibody is produced by a hybridoma formed by fusion of cells from a mouse myeloma cell line and spleen cells from a mouse previously immunized with human mononuclear cells.

* * * * *